United States Patent [19]

Fritts et al.

[11] 4,380,926
[45] Apr. 26, 1983

[54] BATTERY ELECTRODE HARDNESS TESTER

[75] Inventors: David H. Fritts, Dayton; John F. Leonard, Xenia, both of Ohio

[73] Assignee: The United States of America as represented by the Secretary of the Air Force, Washington, D.C.

[21] Appl. No.: 227,564

[22] Filed: Jan. 22, 1981

[51] Int. Cl.$^3$ .............................................. G01N 3/44
[52] U.S. Cl. .......................................................... 73/83
[58] Field of Search ............................................ 73/83

[56] References Cited

U.S. PATENT DOCUMENTS

| | | | |
|---|---|---|---|
| 2,022,040 | 11/1935 | James | 265/12 |
| 2,030,855 | 2/1936 | Canfield | 265/12 |
| 2,039,563 | 5/1936 | Simonds | 265/14 |
| 2,182,235 | 12/1939 | Polushkin | 265/16 |
| 2,226,600 | 12/1940 | Eddington | 265/13 |
| 2,938,377 | 5/1960 | Sklar | 73/83 |
| 2,975,630 | 3/1961 | Michel | 73/78 |
| 3,221,535 | 12/1965 | Ohishi | 73/83 |
| 3,513,691 | 5/1970 | Aston et al. | 73/83 |
| 3,590,630 | 7/1971 | Ericksson | 73/83 |
| 3,899,931 | 8/1975 | Iwasaki | 74/34 |
| 4,182,164 | 1/1980 | Fohey | 73/83 |

Primary Examiner—Herbert Goldstein
Attorney, Agent, or Firm—Donald J. Singer; Jacob N. Erlich

[57] ABSTRACT

A unique electrode plaque hardness tester, and a method of testing for the hardness of an electrode plaque specimen, are taught. The hardness tester is of the indentation type, and permits the hardness testing of an electrode plaque that is very thin (e.g., 0.75 mm) and that is made of non-homogenous, sintered material, such as a nickel electrode plaque. A fixed load, comprising a lesser first load and a larger second load, is applied in sequence to a test specimen of the electrode plaque, with two superimposed indentations resulting. The hardness of the electrode plaque, as a result of the use of this tester, is inversely related to the difference in the depths of the two indentations. Data acquired as a result of testing specimens with this hardness tester establishes that the harder the electrode plaque is, the less efficient is the performance of an active battery electrode which includes this electrode plaque.

3 Claims, 4 Drawing Figures

4,380,926

BATTERY ELECTRODE HARDNESS TESTER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to hardness testers of the indentation type and, more particularly, to a device which is capable of testing the hardness of a nickel battery electrode and, more specifically, the hardness of electrode plaque.

Currently, more and more emphasis is being placed upon the development of high performance, compact, lightweight, miniaturized power sources. Such power sources generally are in the form of high-quality, nickel-cadium, nickel zinc, and nickel-hydrogen cells or batteries. Such batteries have many applications, although their primary application is in use as an aircraft emergency power source and/or spacecraft power source.

Historically, however, there has been little interest in the mechanical characteristics of the sintered battery electrode substrate material, more commonly referred to as electrode plaque or simply by the term plaque. This substrate (plaque) has been characterized primarily in terms of its chemical compatibility, porosity, current carrying capability and surface area. Plaque has commonly been viewed as merely an immobile and inert "container" for the active chemical components or chemically active electrode material.

Recently attention has been given by us to the fatigue characteristics of the electrode plaque, because fatigue has been shown to result in long term capacity degradation of nickel electrodes. An example of a battery electrode fatigue simulator can be found in U.S. patent application Ser. No. 227,565, filed by us on Jan. 22, 1981. In addition, we have investigated plaque hardness, and have found that hardness affects the short term capacity characteristics and utilization efficiency of electrodes. In essence, we have determined that the harder the plaque is, the poorer the electrode will perform. The effect of this conclusion is that it implies that the electromechanical process occurring is not independent of the substrate mechanical characteristics. This is particularly important in the Ni-H$_2$ battery in which the life-limiting component of the battery is the nickel electrode. Consequently, the plaque configuration and mechanical properties (including hardness) must be engineered to obtain maximum efficiency and life from the nickel electrode.

Currently available hardness testing equipment, such as the Brinell and Rockwell testers are inadequate for electrode plaque hardness testing for a number of obvious reasons, including the thinness (i.e., 0.75 mm) of the normally used electrode plaque, and the non-homogenous, sintered structure of the electrode plaque.

It is, therefore, readily apparent that what is needed in the art, and is not currently available, is a device with which the relative hardness of the electrode plaque (and other very thin specimens of non-homogenous, sintered material) can be tested and ascertained for contemplated potential use of the particular electrode plaque (s), and additionally for use in the quality control of electrode plaques and other similar materials.

SUMMARY OF THE INVENTION

The instant invention permits the hardness testing of a battery electrode (including nickel electrode plaque), and thereby fulfills the above-mentioned need. Therefore, this unique hardness tester constitutes a significant advance in the state-of-the-art.

Accordingly, the principal object of this invention is to provide a device for testing and ascertaining the relative hardness of a battery electrode, including an electrode plaque which is very thin (e.g., 0.75 mm) and is made of non-homogenous, sintered material.

Another object of this invention is to provide a battery electrode hardness tester by which the relative hardness of the electrode can be ascertained quickly and accurately.

A further object of this invention is to provide a battery electrode hardness tester of the indentation type which is useable even if the electrode is very thin (e.g., 0.75 mm) and is made of sintered, rather than homogenous material.

A still further object of this invention is to provide a battery electrode hardness tester which can be used by persons who do not have any special technical skills.

Still yet another object of this invention is to provide a battery electrode hardness tester which is economical to manufacture, and which utilizes conventional, currently available components that lend themselves to standard mass producing manufacturing techniques.

These objects of this invention, as well as other objects related thereto, will become readily apparent after a consideration of the description of the invention, together with reference to the contents of the Figures of the drawing.

DESCRIPTION OF THE DRAWING

FIG. 3 is a graphic representation of the quantitative results, obtained in part with the use of this invention, of the relative hardness of electrode plaque as compared to the utilization efficiency of the electrode plaque, showing that the harder plaque limits the electrode performance.

DETAILED DESCRIPTION OF THE PREFERRED EMBODIMENT

It has been established that the mechanical hardness characteristics of battery electrode plaque are related to utilization efficiency characteristics of the active battery electrode. Therefore, before setting forth in detail the description of this invention, it is necessary to more clearly define the terms battery electrode and plaque. In general, the distinction between the electrode plaque and the active electrode is as follows: The electrode plaque is the electrode chemically inactive substrate in which the active chemical components are impregnated. In other words, a chemically impregnated plaque is an active battery electrode. In general, plaque consists of a sintered nickel sponge that is typically 90% porous, and in which there is an internal current collection screen which is made of nickel and which is sintered to the sponge. It should, however, be realized that in conventional usage the terms "electrode" and "plaque" may be used interchangeably. Therefore, although the following description incorporates the proper usage of the terms, interchanging the terms "electrode" and "plaque" does not destroy the inventive concept set forth in detail hereinbelow.

Figure 1:
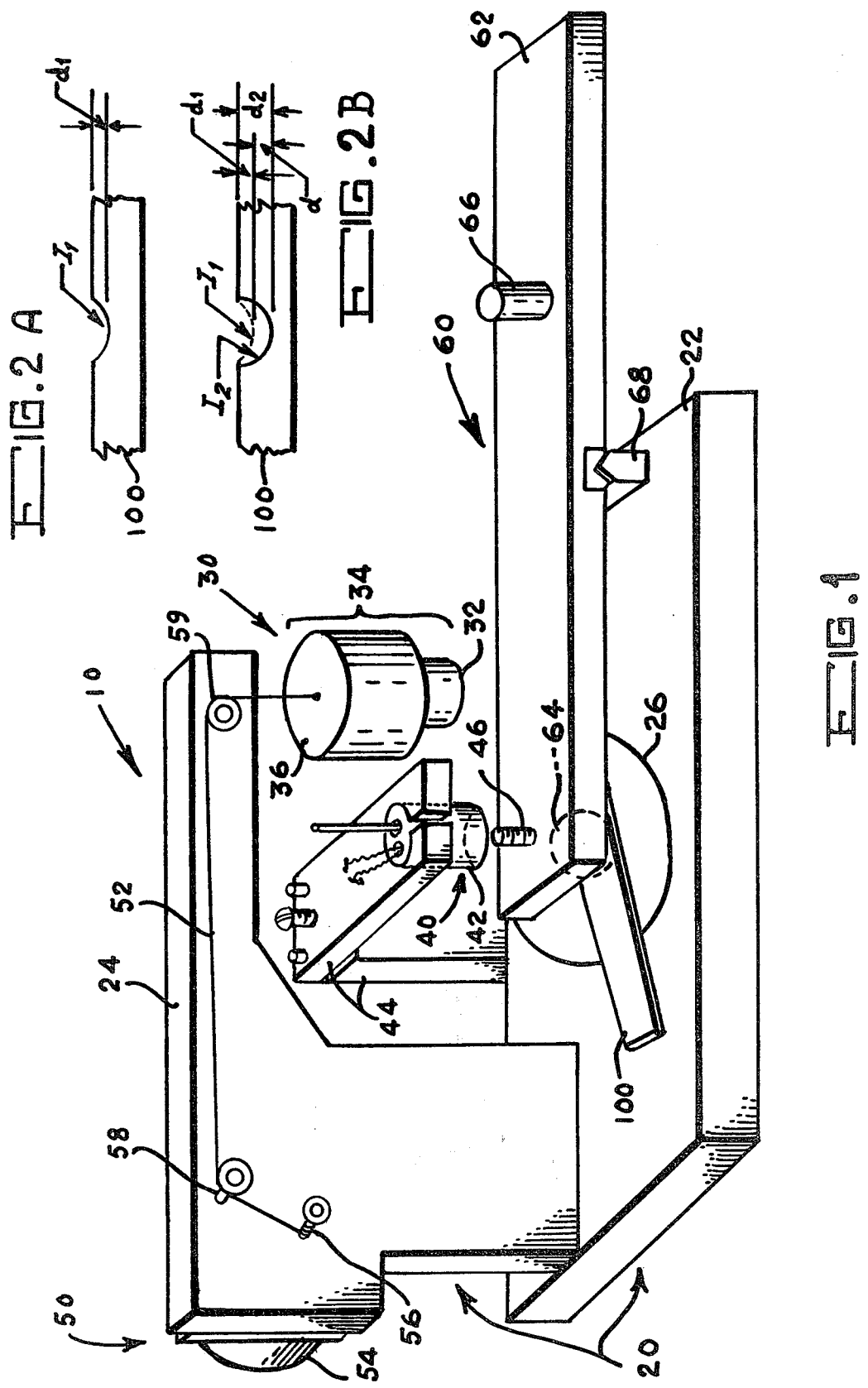
FIG. 1 is a front view, in simplified pictorial and schematic form, and partially in perspective, of the preferred embodiment of the invention.

With reference to FIG. 1, therein is shown a preferred embodiment 10 of our inventive battery electrode hardness tester of the indentation type. Also shown therein is a specimen 100 of a battery electrode, such as an electrode plaque which, it is to be remembered, is very thin (e.g., 0.75 mm) and is made of non-homogenous material (e.g., sintered material). The specimen 100 is depicted in FIG. 1 as positioned on the tester 10, ready for hardness testing.

With reference to FIGS. 2A and 2B, therein is shown specimen 100 after it has undergone the two phases of testing for hardness with the use of our tester 10. It is to be remembered that the specimen is very thin (e.g., 0.75 mm) and is made of non-homogenous or porous material, such as sintered material.

Figure 2:
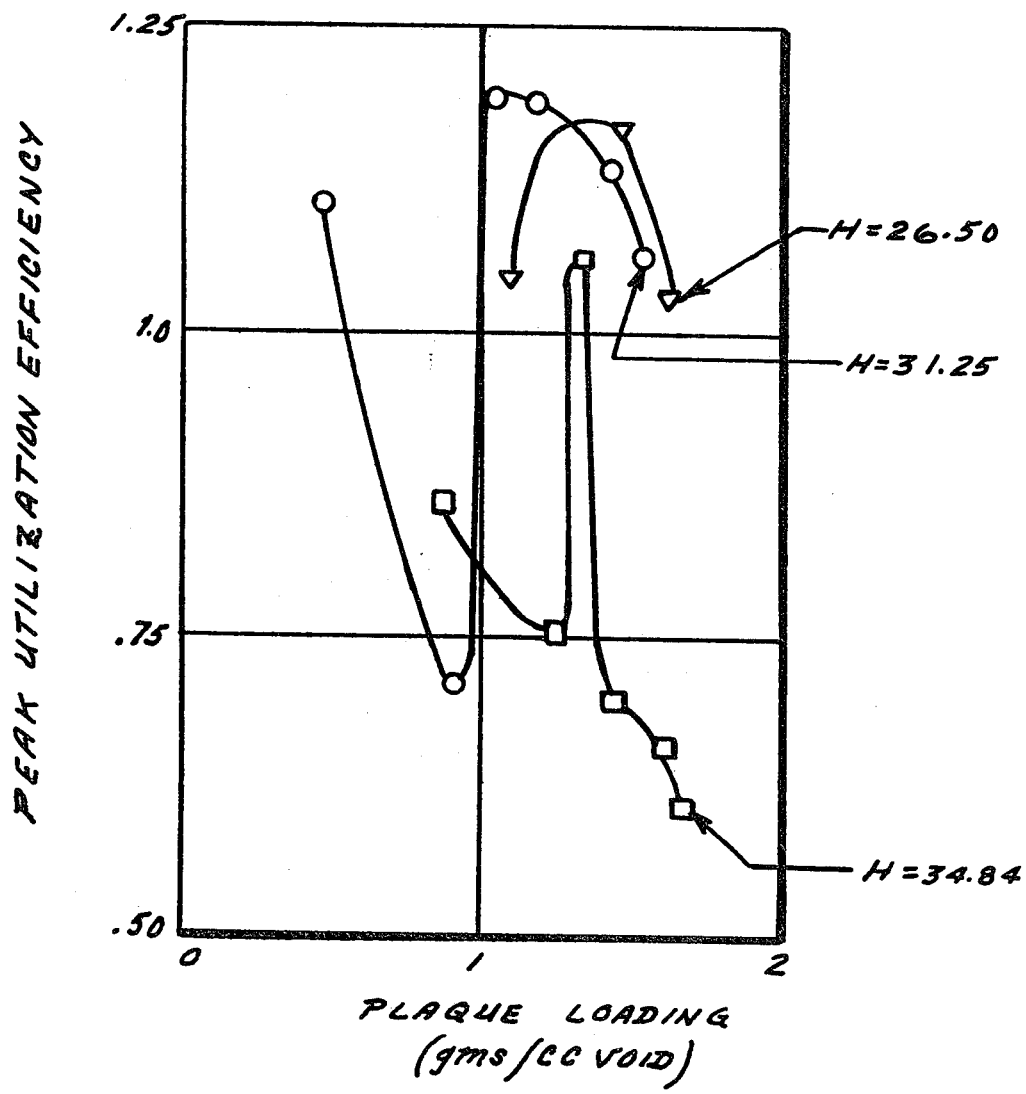
FIGS. 2A and 2B are simplified pictorial and schematic representations enlarged and not to scale, of the result of applying to a specimen of the material to be tested (e.g., a battery electrode, or an electrode plaque) a first load and a larger second load.

Now, with reference to both FIGS. 1 and 2, in the most basic and generic structural form, the inventive hardness tester 10, FIG. 1, comprises: a frame (such as is generally designated 20, FIG. 1) which includes a base member 22 upon which is positioned and supported the specimen 100 of a battery electrode that is to be tested for hardness, and an overhang member 24 connected to the base member 22, such that the two members 22 and 24 form a support structure; means (generally designated 30, FIG. 1), operatively connected to the frame 20 and in contact with the specimen 100, for applying in sequence a first preselected load 32 (i.e., a tare load or tare weight) and a second preselected load 34 (i.e. a combination load, test load, or test weight), which includes the weight of the first load 32 and therefore of course is greater than the first load 32, such that a first indentation $I_1$, FIG. 2A, is formed in the specimen 100 by the application of the first load 32 and a second indentation $I_2$, FIG. 2B, is formed in the specimen 100 by the application of the second load 34; and, means (generally designated 40, FIG. 1) for measuring the depth $d_1$, FIG. 2A of the first indentation $I_1$, FIG. 2A, and the depth $d_2$, FIG. 2B, of the second indentation $I_1$, FIG. 2B, so that the difference d, FIG. 2B, between the depths $d_1$, FIG. 2A and 2B, and $d_2$, FIG. 2B, can be ascertained. The relative hardness of any specimen, such as 100, FIGS. 1 and 2, is inversely related to the difference d, FIG. 2B, in depths $d_1$ and $d_2$.

More specifically, the loads applying means 30, FIG. 1, includes: the aforementioned first weight 32, which is used in applying the first preselected load, and which preferably is cylindrical in shape, and made of brass; a second weight 36, FIG. 1, in the form of a brass hollow cylinder attached to and surrounding the first weight 32, such that these two combined weights 32 and 36 constitute the second load (or combined load or test load) 34 which is applied to the specimen 100 after the application of the first load 32; a drive means (generally desingated 50, FIG. 1) for applying the first and second loads 32 and 34, with this drive means 50 connected to the first and second weight 32 and 36 by suitable conventional means, such as weight or lock support line 32; and means (generally designated 60, FIG. 1), adjacent to the weights 32 and 34, for transmitting the first and second loads 32 and 34 from the first and second weights 32 and 36 to the specimen 100.

It is here to be noted that the drive means 50, FIG. 1, preferably also includes a drive motor, such as reversible electric motor 54, FIG. 1, to which is connected drive shaft (or wind-up drum) 56. It is also to be noted that the weight or load support line 52 interconnects the reversible drive motor 54 (and the drive shaft 56 thereof) to the weights 32 and 36 (and the loads 32 and 34), and the line 52 in turn is supported and guided by support guides 58 and 59.

The means 60, FIG. 1, for transmitting the first and second loads 32 and 34 from the first and second weights 32 and 36 to the specimen 100 includes: an arm or beam 62 balanced on the base member 22 of the frame 20, with the beam having an indentation-forming member 64 connected (such as with an adhesive) to one end of the balanced beam 62, and with the indentation-forming member 64 being in contact with the specimen 100. As a matter of preference and not of limitation, the indentation-forming member 64 is a steel ball. The means 60 further includes a counterweight 66 on the beam 62, and an anvil or knife-edge type fulcrum member 68 in contact with the beam 62 and positioned intermediate the indentation ball 64 and the counterweight 66, with the fulcrum member 68 attached to the base member 22.

The means 40, FIG. 1, for measuring the depth $d_1$, FIGS. 2A and 2B, of the first indentation $I_2$ (which is caused by the first weight or load 32), and for measuring the depth $d_2$, FIG. 2B, of the second indentation $I_2$ (which is caused by the combined weight 32 and 36 or the load 34), and thereby determining the difference d, FIG. 2B, between the respective depths $d_1$ and $d_2$ includes a suitable conventional displacement measuring device 42 (preferably a linear voltage displacement transducer. i.e., LVDT), which is positioned over the indentation ball 64, by being held and releasably supported by a bracket 44 that is connected to the base member 22. Simultaneously, the transducer 42 is in contact with the beam 62 by use of a suitable conventional interconnection means, such as beam-to-transducer inter-connection stud 46.

It is to be noted that we also teach herein a method of testing the hardness a specimen 100, FIG. 1, of a battery electrode, and that the contents of the Figures of the drawing show, in their totality, the results of practicing the steps of our inventive method.

The fundamental steps of our method are listed below in their preferred sequence.

Firstly, positioning the specimen 100 on a support (such as base member 22, or platform 26 which is attached to base member 22) in contact with a means 30 for applying, in sequence, a first preselected compression load 32 and a second preselected compression load 34, with the second load 34 being greater than the first load 32. As can be seen from FIG. 1, the second load comprises second weight 36 and first load or weight 32. Additionally, as can be seen from FIG. 1, and as hereinbefore described, the means 30 further includes the drive means 50 and the load transmitting means 60.

Next, applying the first preselected compression load 32 to the specimen 100, whereby a first indentation $I_1$, FIGS. 2A and 2B, with a depth of $d_1$ is formed in the specimen 100.

Then, measuring the depth $d_1$. This is done with the transducer 42.

Next, applying the second and greater preselected compression load 34 to the specimen 100, whereby a second indentation $I_2$, FIG. 2B, with a depth of $d_2$ is formed in the specimen 100.

Then, measuring the depth $d_1$. This also is done with the use of transducer 42.

Next, the difference in depths d, FIG. 2B, is ascertained by suitable means, such as a null calibrated meter (not shown), or simply by measurement and subtraction.

The result is that the relative hardness of the specimen is represented by, and is inversely related to, the difference d in the depth $d_2$ and $d_1$, such that the specimen is relatively hard if the difference of the depth is relatively small, whereas the specimen is relatively less hard if the difference of the depths is relatively great.

It is to be remembered that the method is useable with a specimen 100 which is a battery electrode and, most particularly, with a battery electrode that is very thin (e.g., 0.75 mm) and is non-homogenous and sintered in structure, such as an electrode plaque.

MANNER OF USE OF THE PREFERRED EMBODIMENT

The manner of use, and of operation (i.e., function), of the preferred embodiment of the inventive battery electrode hardness tester 10, FIG. 1, can be easily ascertained by any person of ordinary skill in the art from the foregoing description, coupled with reference to the contents of the Figures of the drawing, particularly FIGS. 1 and 2.

For others, the following simplified explanation is given. The device 10 is an indentation type tester, i.e., a fixed load 34 is applied and the distance that the steel ball 64 is depressed into the specimen or sample 100 is a measure of the hardness of that test specimen or sample.

The hardness is defined as $$H = (1/d)$$

where d, FIG. 2B, is the difference in indentation depths (i.e., $d_2-d_1$) in millimeters.

To apply the test load 34, the specimen 100 is placed under the ball 64 which, in turn is attached to the balance arm 62. The load on the specimen 100 from the balance arm 62 per se is preferably 2 grams. This balance arm load was obtained by precise placement of the counterweight 66 on the balance arm 62. Once the test specimen 100 is in place, the combined load 34 (the "tare" or first weight 32, and the "test" weight or second weight 36) is lowered by use of the reversible drive motor 54, the interconnecting motor-to-weight line 52, and the line support guides 58 and 59. The tare weight 32 first contacts the balance arms, placing a 100 gram load on the specimen 100. The depth $d_1$, FIGS. 2A and 2B, of indentation $I_1$, FIGS. 2A and 2B, is taken as the zero, or the null, point or level. Next, the second weight 36 contacts the balance arm 62, so that a total weight or combined load 34 of 500 grams is on the specimen 100, with the tare weight 32 nesting up into the hollow second weight 36. The depth of $d_2$, FIG. 2B, of the indentation $I_2$ is caused by the test load 34. The difference of the depths $d_2$ and $d_1$ is d, FIG. 2B, and is used in the above-described hardness formula. To remove the test specimen 100, the drive motor 54 is reversed, and the weights 32 and 36 are repositioned for use with the next test specimen.

As a matter of preference, but not of necessity, and out of an abundance of precaution, this procedure or method is used about seven (7) times per test specimen, and the average value of d, FIG. 2B, is used.

To measure the indentation depths $d_1$ and $d_2$, FIGS. 2A and 2B, the transducer 42 is used in conjunction with a strip chart recorder (not shown). The sensitivity of this arrangement is about $2.5 \times 10^{-5}$ mm, whereas a characteristic depth in nickel electrode plaque 100 is about 0.02 mm. Thus, this measuring (sensing) system 40 is more than adequate.

Now, with reference to FIG. 3, the graphic representation of the quantitive results, obtained in part with the use of our hardness tester 10, of the relative hardness of nickel electrode plaque as compared to the utilization efficiency plaque as compared to the utilization efficiency of the electrode plaque, were obtained by cycling each nickel electrode in a Ni/Cd test cell until the maximum utilization was observed (i.e., 80 cycles or greater). The cell was discharged to 0.4 volts on each cycle, and a Cd third electrode was used to assure the cell remained nickel limited. The maximum utilization is interpreted in FIG. 3 to represent the best electrochemical performance of which the test electrodes are capable. With this interpretation, it is concluded from the contents of FIG. 3 that the harder plaque limits the electrode performance. Stated another way, the less hard that the electrode plaque is, the better is its performance.

CONCLUSION

It is abundantly clear from all of the foregoing, and from the contents of the Figures of the drawing, that the stated objects of the invention, as well as objects related thereto, have been achieved.

It is to be noted that, although there have been described and shown the fundamental and unique features of our inventive hardness tester 10, as applied to a preferred embodiment and as adapted for use in a particular application (i.e., the hardness testing of nickel electrode plaque 100), various other embodiments, variations, adaptations, substitutions, additions, omissions, and the like may occur to, and can be made by, those of ordinary skill in the art. For example: the indentation member 64 need not be a steel ball, and can be of a different shape, size, and material; the size and material of the weights 32 and 36 can be changed; and, the displacement sensing means 40 need not include a transducer 42, and may instead include appropriate optical means.

Additionally, because of our teachings herein, it may occur to others of ordinary skill in the art that, in appropriate particular circumstances, the number of the basic and fundamental steps of our inventive method can be increased, decreased, or otherwise varied, and/or that their sequence can be changed. In this regard it is to be noted that, in spite of any variations in the number or sequence of the steps of our method, the same disclosed, desired, end results will be obtained, nevertheless.

What is claimed is:

1. A method of testing relative hardness of a specimen of an electrode plaque which is of a thickness of approximately 0.75 mm and which is made of a non-homogenous, sintered material in order to establish electrode performance, said method comprising the steps of:

a. positioning said specimen on a support in contact with a means for applying, in sequence, a first preselected compression load and a second preselected compression load, with said second preselected load being greater than said first preselected load, b. applying said first preselected compression load to said specimen, whereby a first indentation is formed thereby in said specimen;

c. measuring the depth of said first indentation;

d. applying said second preselected greater compression load to said specimen, whereby a second indentation is formed thereby in said specimen, with said second indentation located in a superimposed positioned on said first indentation; and e. measuring the depth of said second indentation;

(f) determining a difference in said depths;

(g) determining the relative hardness of said specimen by analyzing said differences in said depths, said relative hardness being inversely related to said difference in said depths, in that said specimen is relatively hard if said difference in said depths is relatively small, whereas said specimen is relatively less hard if said difference in said depths is relatively great, and (h) determining electrode performance by directly relating said relative hardness to better electrode performance.

2. An electrode plaque hardness tester of the indentation type for use in testing the hardness of an electrode plaque specimen which is of a thickness of approximately only 0.75 mm and which is made of a non-homogenous, sintered material, said electrode plaque hardness tester comprising:

a. a frame, including a base member upon which is positioned said specimen of said electrode plaque to be tested for hardness;

b. means, operably connected to said frame and in contact with said specimen, for applying in sequence a first preselected compression load and a second preselected compression load on said specimen, with said second load being greater than said first load, whereby a first indentation is formed in said specimen by said first load and a second indentation, superimposed on said first indentation, is formed in said specimen by said second load, wherein said compression loads applying means includes:

a first weight of approximately 100 grams which is used in applying said first preselected compression load;

a second weight of approximately 400 grams attached to said first weight, wherein said first and second weights are used together in applying said second preselected compression load;

a drive means for applying said first and second preselected compression loads, with this means connected to said first and second weights, and wherein this means includes a reversible drive motor, and a weight-support line interconnecting said drive motor and said first and second weights; and means, adjacent said weights and said specimen, for transmitting said first and second compression loads from said first and second weights to said specimen, wherein this means includes a beam balanced on a knife-edge type fulcrum member on said base member of said frame, to allow repeatability to be within a fraction of a gram, with said beam having an indentation-forming member rigidly connected to one end thereof to prevent affecting repeatability, and with said indentation-forming member in contact with said specimen; and c. means for measuring the depth, respectively, of said first indentation and of said second indentation, thereby a difference between the respective depths is ascertained, and wherein this means includes a linear voltage displacement transducer;

whereby relative hardness of said specimen is represented by, and is inversely related to, said difference in said depths, in that said specimen is relatively hard if such difference in said depth is relatively small, whereas said specimen is relatively less hard if said difference in said depths is relatively great.

3. An electrode plaque hardness tester, as set forth in claim 2, wherein said indentation-forming member is a steel ball fixedly attached to said one end of said balanced beam.

* * * * *